United States Patent [19]

Vogt et al.

[11] Patent Number: 5,250,441

[45] Date of Patent: Oct. 5, 1993

[54] METHOD FOR KIT FOR ESTIMATING THE AMOUNT OF METHYL ANTHRANILATE

[76] Inventors: Peter F. Vogt, 239 Woodcrest Dr., Loveland, Ohio 45140; Bruce Becraft, 7350 Blue Ash Rd., Cincinnati, Ohio 45236

[21] Appl. No.: 2,192

[22] Filed: Jan. 8, 1993

[51] Int. Cl.⁵ ............................................. G01N 33/00
[52] U.S. Cl. .................... 436/111; 436/106; 436/19; 422/61
[58] Field of Search ................. 422/61; 436/111, 106, 436/19

[56] References Cited

U.S. PATENT DOCUMENTS 3,907,769  9/1975  Dehnert et al. ...................... 260/156
5,200,330  4/1993  Page et al. ............................ 435/128

Primary Examiner—James C. Housel
Assistant Examiner—N. Bhat
Attorney, Agent, or Firm—James M. Verna

[57] ABSTRACT

A method and kit for estimating the amount of methyl anthranilate includes obtaining a sample suspected of having methyl anthranilate, acidifying the sample with a strong acid, adding sodium nitrite to the acidified sample producing nitrous acid which in the presence of methyl anthranilate produces a diazonium ion. The method further comprises a step of adding sulfamic acid which removes excess nitrous acid from the sample, followed by the addition N-(1-naphthyl) ethylenediamine which reacts with the diazonium ion to form a colored complex which is color responsive which is then compared to standards prepared using known amounts of methyl anthranilate. The kit provides the a sample holder and vials of ingredients and standards to practice the method.

6 Claims, No Drawings

METHOD FOR KIT FOR ESTIMATING THE AMOUNT OF METHYL ANTHRANILATE

BACKGROUND OF THE INVENTION

1. Field of the Invention

The present invention relates to a method and kit for estimating the amount of methyl anthranilate in water in the field.

2. Prior Art

Birds are a concern at airports located near bodies of water or where, after rains or snows, puddles form on runways and other areas. These bodies of water and puddles attract birds which pose a potential danger for the aircraft. Another area of concern is at fisheries, where birds eat the fish. Compounds with bird aversion agents have been developed for use in water. One of the primary bird aversion agents used is methyl anthranilate (MA). However, in order to remain effective, the MA must be maintained at a certain concentration. The prior art lacks a simple method and kit for estimating the amount of methyl anthranilate in water in the field.

SUMMARY OF THE INVENTION

The present invention is concerned with a method for estimating the amount of methyl anthranilate (MA) in water. This method comprises the steps of obtaining a sample suspected of having methyl anthranilate; acidifying the sample with a strong acid; adding sodium nitrite to the acidified sample producing nitrous acid which in the presence of MA produces a diazonium ion; adding a reagent to remove excess nitrous acid; adding N-(1-naphthyl)ethylenediamine which reacts with the diazonium ion to produce a measurable color response; and comparing the obtained color response to standards prepared using known amounts of MA.

In addition, the present invention relates to a kit for estimating the amount of methyl anthranilate (MA) in water. The kit comprises a first container means for holding a sample suspected of having methyl anthranilate; a second container means for holding a strong acid; a third container means for holding sodium nitrite; a fourth container means for holding N-(1-naphthyl)ethylenediamine; a fifth container means for holding a reagent for removing excess nitrous acid; and standards having differing amounts of methyl anthranilate in solution for comparison.

DETAILED DESCRIPTION OF INVENTION

As used herein, the terms "bird(s)" refers to members of the class "Aves".

This method is suitable for the estimation of methyl anthranilate (MA) in water, providing the absence or near absence of particulates or soluble colorants.

In the preferred method, the samples are acidified with a strong acid, diazotized with nitrous acid, the excess nitrous acid removed with an appropriate reagent, and the resulting diazonium ion coupled with N-(1-naphthyl)ethylenediamine to produce a measureable colored azo dye. The intensity of the dye so produced is compared to standards prepared using known amounts of MA.

An example of a strong acid is 1N HCl.

N-(1-naphthyl)ethylenediamine was found to be superior over other potential colorimetric agents for the detection of MA for several reasons. The reagent is extremely sensitive to MA around 100 ppb. This reagent, unlike all others, can be used at very low pH. For MA, this has two major advantages. First, stability of the diazonium function is not jeopardized by having to adjust the pH above 5 with a buffer as is the case for other classic coupling agents such as beta-naphthol. Also precluded at low pH is the hydrolysis of the ester group to form anthranilic acid (AA) diazo which might affect the intensity or quality of the color formed.

Although others have used this reagent for the determination of MA through diazotization and coupling, the present method employs the advantage of removing excess nitrous acid with the appropriate reagent before the coupling step. It was determined that nitrous acid reacts with the reagent, presumably diazotizing it. The diazotized reagent, being an aliphatic diazonium compound, is not stable and rapidly decomposes to unknown highly colored compounds. The use of a nitrous acid removing reagent therefore insures sensitivity and the stability and quality of the color formed with MA-diazo. An example of an appropriate nitrous acid removing reagent is sulfamic acid.

By way of example only, the following procedure is provided to illustrate the method as well as enable one skilled in the art to be able to produce the components of a kit.

Preparation of Reagents

Sodium nitrite reagent: $0.24 \pm 0.02$ grams of 38% sodium nitrite is put into a 100 ml flask, and diluted to the 100 ml mark with distilled water.

Sulfamic acid reagent: 1.5 grams of sulfamic acid are dissolved in about 50 ml distilled water in a flask.

N-(1-naphthyl)ethylenediamine reagent (color development reagent): $0.35 \pm 0.01$ g of N-(1-naphthyl)-ethylenediamine are put into a 100 ml volumetric flask and dissolved using a mixture of 90/10 water/methanol. Approximately 1 ml of 1N HCl is added and then dilute to the mark with mixed solvent.

Preparation of Standards 100 ppm MA stock solution: $13.2 \pm 0.2$ mg MA hydrogen sulfate is put into a 100 ml volumetric flask and diluted to the mark with distilled water.

50 ppm, MA solution: dilute 100 ppm stock solution (50 to 100 ml) with distilled water.

10 ppm MA solution: dilute 100 ppm stock solution (10 to 100 ml) with distilled water.

For each standard solution take 1 ml and transfer to a clear vial. Add, in order: 1 ml 1N HCl, 1 ml sodium nitrite solution, 5 drops sulfamic acid solution and finally 1 ml of N-(1-naphthyl)-ethylenediamine reagent. Stir well by swirling the vial after the addition of each solution. If needed, a 200 ppm standard may be prepared by using 2 ml of the 100 ppm stock solution.

Allow the solution to stand at room temperature for 15-30 minutes, then dilute to the top of the vial with distilled water. Cap vials. These standards should be suitable for comparison standards for at least a week. When stored in a dark refrigerator, this shelf life is considerably extended. The N-(1-naphthyl)-ethylenediamine reagent's shelf life can also be extended by storing in the dark and cold. However, the reagent should be brought to room temperature before using as it could adversely affect the kinetics of the color development reaction if cold.

Sample Solutions

Treat 1 ml sample solutions with the reagents as described above for preparing standards. Pretreat the samples by filtering through a 0.2 micrometer filter if necessary to remove particulates which might interfere with the intensity of the color formed. Compare samples to the prepared standards to estimate the concentration of MA in the sample.

Lastly, the present invention relates to a kit for estimating the amount of methyl anthranilate (MA) in water. The kit comprises a first container means for holding a sample suspected of having methyl anthranilate; a second container means for holding a strong acid; a third container means for holding sodium nitrite; a fourth container means for holding N-(1-naphthyl)ethylenediamine; a fifth container means for holding a reagent for removing excess nitrous acid; and standards having differing amounts of methyl anthranilate in solution for comparison. An example of a strong acid is 1N HCl. An example of a reagent for removing excess nitrous acid is sulfamic acid.

The foregoing description of the invention has been made with references with a few preferred embodiments. Persons skilled in the art will understand that changes and modifications can be made in the invention without departing from the spirit and scope of the claims as follows.

We claim:

1. A method for estimating the amount of methyl anthranilate (MA) in water, comprising the steps of:
   a) obtaining a sample suspected of having methyl anthranilate (MA);
   b) acidifying the sample with a strong acid;
   c) adding sodium nitrite to the acidified sample producing nitrous acid which in the presence of methyl anthranilate produces a diazonium ion;
   d) adding a reagent to remove excess nitrous acid;
   e) adding N-(1-naphtyl)ethylenediamine which reacts with the diazonium ion to produce a measurable color response; and
   f) comparing the obtained color response to standards prepared using known amounts of methyl anthranilate to estimate the amount of methyl anthranilate in said sample.

2. The method of claim 1, wherein the reagent to remove excess nitrous acid is sulfamic acid.

3. The method of claim 1, wherein the strong acid is HCl.

4. A kit for estimating the amount of methyl anthranilate (MA) in water, comprising:
   a container means for holding a sample suspected of having methyl anthranilate;
   a second container holding a strong acid;
   a third container holding sodium nitrite;
   a fourth container holding N-(1-naphthyl)ethylenediamine;
   a fifth container holding a reagent for removing excess nitrous acid; and
   standards having differing amounts of methyl anthranilate in solution for comparison.

5. The kit of claim 4, wherein the reagent for removing excess nitrous acid is sulfamic acid.

6. The kit of claim 4, wherein the strong acid is HCl.

* * * * *